United States Patent [19]

Bowers

[11] Patent Number: 4,540,830

[45] Date of Patent: Sep. 10, 1985

[54] ANTI-JUVENILE HORMONES

[75] Inventor: William S. Bowers, Geneva, N.Y.

[73] Assignee: Cornell Research Foundation, Inc., Ithaca, N.Y.

[21] Appl. No.: 389,135

[22] Filed: Jun. 16, 1982

Related U.S. Application Data

[62] Division of Ser. No. 239,745, Mar. 2, 1981, Pat. No. 4,347,256.

[51] Int. Cl.³ .............................................. C07C 43/02
[52] U.S. Cl. .................................................... 568/651
[58] Field of Search ................ 560/144, 254; 568/648, 568/651

[56] References Cited

U.S. PATENT DOCUMENTS

| | | |
|---|---|---|
| 2,359,311 | 10/1944 | Hromatka . |
| 2,829,123 | 4/1958 | Tawney . |
| 3,349,113 | 10/1967 | Gloor et al. . |
| 3,564,025 | 2/1971 | Folkers et al. . |
| 3,929,904 | 12/1975 | De Simone et al. ................ 568/648 |
| 4,039,573 | 8/1977 | Kijima et al. . |
| 4,072,660 | 2/1978 | Muller et al. . |
| 4,137,273 | 1/1979 | Siddall ................................ 568/648 |
| 4,192,949 | 3/1980 | Merger et al. . |

FOREIGN PATENT DOCUMENTS

| | | |
|---|---|---|
| 0012157 | 6/1980 | European Pat. Off. ............ 568/654 |
| 0018118 | 10/1980 | European Pat. Off. .............. 568/67 |
| 54-145530 | 11/1979 | Japan .................................... 568/648 |
| 928162 | 6/1963 | United Kingdom ................ 568/648 |

OTHER PUBLICATIONS

Berger, Journ. Pharmacol. Exptl. Therap., vol. 93, pp. 470–481 (1948), p. 474 pertinent.
Chem. Abstracts, 47: 120 (1953).
Chem. Abstracts, 93: 168127r (1980).
Chem. Abstracts, 95: 132609b (1981).
Chem. Abstracts, 97: 124461y (1982), same as Science 217.
Bowers, W. S. et al, Science, 217 (4560), pp. 647–648 (1982).

*Primary Examiner*—Ethel G. Love

[57] ABSTRACT

This invention relates to substituted isopentenyl phenyl compounds and their use as anti-juvenile hormones. The compounds have been found effective in the control of insects by inhibiting the actions of juvenile hormones. Such compounds act to induce precocious maturation of immature insects resulting in a reduction in the ecological impact of the insect. Additional effects which have been obtained include sterilization of mature insects. Based on previous research it is also believed these compounds will cause interruption of embryogenesis in insect eggs, the induction of diapause in insects and the prevention of sex pheromone secretion in insects.

1 Claim, No Drawings

ANTI-JUVENILE HORMONES

This is a division of application Ser. No. 239,745, filed Mar. 2, 1981, now U.S. Pat. No. 4,347,256.

The compounds of the invention correspond to the formula:

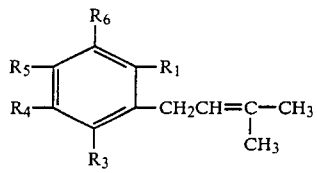
(IA)

where $R_1$ and $R_5$ are independently hydrogen; straight or branch chain lower alkyl having 1-4 carbon atoms, or alkenyl having 2-4 carbon atoms;

where $R_2$ is straight or branch chain lower alkyl containing 1-6 carbon atoms; —X—$R_7$, where X is 0 or S and $R_7$ is hydrogen, straight or branch chain lower alkyl, alkenyl or lower alkynyl containing 1-4 carbon atoms; or

where $R_8$ and $R_9$ are independently methyl or ethyl; provided that at least one of $R_1$ and $R_5$ is

or —X—$R_7$, preferably where —X— is 0 and most preferably where —X—$R_7$ is OH; where $R_3$, $R_4$ and $R_6$ are hydrogen or straight or branch chain lower alkyl, alkenyl, alkoxy, alkenoxy or alkynoxy having 1-4 carbon atoms; or where $R_3$ and $R_4$ taken together are

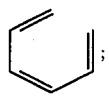

preferably $R_4$ and preferably both $R_4$ and $R_6$, being other than hydrogen. It is most preferred that $R_1$ is —OH or OZ where Z is group hydrolysable under conditions of use to —OH, and that $R_5$ is —$OR_7$.

Preferred compounds of the invention correspond to the formula:

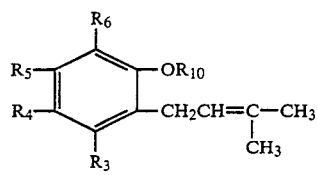
(IB)

where $R_{10}$ is hydrogen, straight or branch chain alkyl or alkenyl (most preferably alkyl) containing 1-4 carbon atoms, or

where $R_2$ is straight or branch chain lower alkyl containing 1-6 carbon atoms;

where $R_4$ and $R_5$ are hydrogen or an organic substituent selected from straight or branch chain lower alkyl, alkoxy alkenoxy or alkynoxy having 1-4 carbon atoms, at least one, preferably $R_5$, and preferably both of $R_5$ and $R_6$ being an organic substituent; and where $R_3$ and $R_6$ are hydrogen or straight or branched chain lower alkyl, alkenyl, alkoxy alkenoxy or alkynoxy having 1-4 carbon atoms.

BACKGROUND OF THE INVENTION

In application Ser. No. 739,886, filed Nov. 8, 1976, the inventor herein disclosed compounds useful as anti-juvenile hormones which were chromenes corresponding to the general formula:

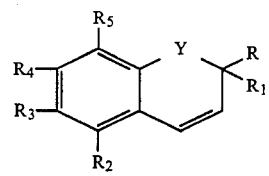

wherein:

R and $R_1$ are H, lower alkyl, straight or branch chain, of about 1 to 4 carbon atoms, lower alkoxy, straight or branch chain, of about 1 to 3 carbon atoms, Cl, Br or F;

$R_2$, $R_3$, $R_4$ and $R_5$ are H, lower alkyl, straight or branch chain, of 1 to 6 carbon atoms, lower alkoxy, straight or branch chain, of 1 to 6 carbon atoms, OH, —$OCH_2OCH_3$, —$OC_2H_4OC_2H_5$, —CO—$OCH_3$, —CO—$OCH_2CH_3$,

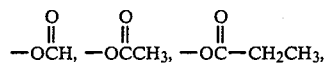

Cl, Br, F, —$SCH_3$, —$SCH_2CH_3$, —$SCH_2CH_2CH_3$, —$NO_2$, dimethylamino, diethylamino, or the structure wherein $R_2$ and $R_3$, or $R_3$ and $R_4$, or $R_4$ and $R_5$ are joined with a —$OCH_2O$—(methylenedioxy) group, or —$OCH_2CH_2$—(ethylenedioxy) group and Y is O, S or NH.

Of the various chemical compounds, other than such anti-juvenile hormones, which have been employed in the prior art as insecticides for controlling insects, many of such prior art compounds have also been found to be harmful to humans and other animal life. In addition, many species of insect pests have developed a resistance and even immunity to available insecticides.

Alternative prior art methods for controlling insects have included the use of hormones, which interfere with the development of insects. Although such hormones have the advantage of apparently being harmless to other animals, their use is generally limited to application relatively late in the insect life cycle, after the insect has already produced its undesirable pest effect.

The endocrine systems of insects secrete a certain hormone known as juvenile hormone which functions to control the biological activities of metamorphosis, reproduction, diapause and sec attractant production. In particular, juvenile hormone functions initially to maintain the young developing insect in an immature condition until it has developed to the point where it is ready to molt to the adult form. When maturation of the insect begins, the body ceases to secrete juvenile hormone until after the insect has passed into the adult form, at which time secretion of juvenile hormone recommences in order to promote the development of the sex organs.

The forms in which juvenile hormone are known to occur in nature are discussed, for example, in the following publications: Trautmann et al., *Z. Naturforsch*, 29C 161-168 (1974); Judy et al., *Proc. Nat. Acad. Sci. USA*, 70, 1509-1513 (1973); Roller et al., Angew. *Chem. Int. Ed. Eng.*, 6, 179-180 (1967); Meyer et al., *Proc. Nat. Acad. Sci. USA*, 60, 853-860 (1968); Judy et al., *Life Sci.*, 13, 1511-1516 (1973); Jennings et al., *Life Sci.*, 16, 1033-1040 (1975); and Judy et al., *Life Sci.*, 16, 1059-1066 (1975).

DESCRIPTION OF THE INVENTION

The present invention is directed to the use of certain substituted isopentenyl phenyl compounds which inhibit the effects of juvenile hormone in insects.

These compounds inhibit the effects of juvenile hormone, during early development of the insect and after reaching adulthood when the sex organs are undergoing development. By so inhibiting the effects of juvenile hormone, early maturation is induced and the fragile insect dies without continuing to fee or reproduce. The compounds of the present invention are also believed useful to interrupt embryogenesis in insect eggs to induce diapause in insects and to prevent sex pheromone secretion in insects. The present compounds may be applied by suitable means including topically, orally or in a vapor state as a fumigant.

The compounds of the invention correspond to the formula:

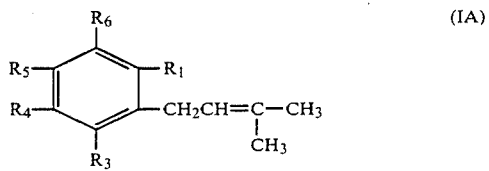

(IA)

where $R_1$ and $R_5$ are independently hydrogen; straight or branch chain lower alkyl having 1-4 carbon atoms, or alkenyl having 2-4 carbon atoms;

wherein $R_2$ is straight or branch chain chain lower alkyl containing 1-6 carbon atoms; $-X-R_7$, where X is O or S and $R_7$ is hydrogen, straight or branch chain lower alkyl alkenyl or lower alkynyl containing 1-4 carbon atoms; or

where $R_8$ and $R_9$ are independently ethyl or ethyl; provided that at least one of $R_1$ and $R_5$ is

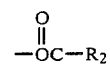

or $-X-R_7$, preferably where $-X-$ is O and most preferably where $-X-R_7$ is OH; where $R_3$, $R_4$ and $R_6$ are hydrogen or straight or branch chain lower alkyl, alkenyl, alkoxy alkenoxy or alkynoxy having 1-4 carbon atoms; or where $R_3$ and $R_4$ taken together are

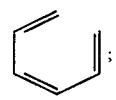

preferably $R_4$ and preferably both $R_4$ and $R_6$, being other than hydrogen.

A group of preferred compounds of the invention correspond to the formula:

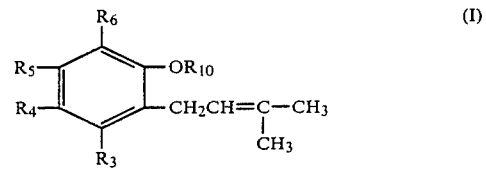

(I)

where $R_{10}$ is hydrogen or

where $R_2$ is straight or branch chain lower alkyl containing 1-6 carbon atoms;

where $R_4$ and $R_5$ are hydrogen or an organic substituent selected from straight or branch chain lower alkyl, alkoxy or alkenoxy having 1-4 carbon atoms, at least one, preferably both of $R_4$ and $R_5$ being an organic substituent, $R_5$ being most preferably alkoxy or alkenoxy; and where $R_3$ and $R_6$ are hydrogen or straight or branch chain lower alkyl, alkenyl, alkoxy or alkenoxy having 1-4 atoms.

Examples of such compounds include:

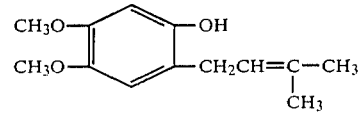

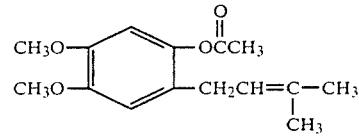

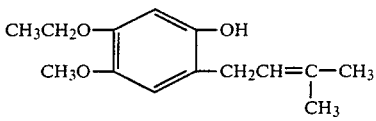

A group of preferred compounds of the invention correspond to the formula:

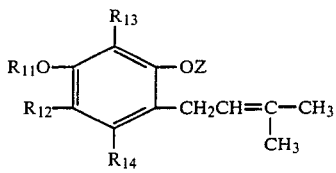

where

Z is most preferably hydrogen or less preferably acetyl or other group readily hydrolysed in vivo to provide the —OH group;

$R_{11}$ is —$CH_3$, $CH_2CH_3$, —$CH_2CH_2CH_3$—$CH(CH_3)_2$, —CH=CH—$CH_3$, —$CH_2$—CH=$CH_2$, $(C_2H_4O)_{1-3}$—$C_2H_5$, —$(C_2H_4O)_{1-3}$—$C_4H_9$;

$R_{12}$, $R_{13}$, and $R_{14}$ are independently H, —$OCH_3$, —$OC_2CH_3$—$OCH_2CH_2CH_3$, —$OCH(CH_3)_2$, —O—CH=CH—$CH_3$, —$OCH_2$—CH=$CH_2$, OCH—C≡CH, —$O(C_2H_4O)_{1-3}$—$C_2H_5$, —$O(C_2H_4O)_{1-3}$—$C_4H_9$, —$CH_3$, $CH_2CH_3$, $CH_2CH_2CH_3$, —$CH_2(CH_2)_2CH_3$, —$CH(CH_3)_2$ provided that $OR_{11}$ and $R_{12}$ taken together can be —O—$CH_2$—$CH_2$—O (ethylenedioxy).

It is most preferred that $R_{11}$ be alkoxyl, most preferably ethoxy and that at least one of $R_{12}$, $R_{13}$ and $R_{14}$, preferably $R_{12}$ be other than hydrogen (with $R_{13}$ or $R_{14}$ where being other than hydrogen preferably being alkyl).

The compounds of the invention can be prepared by a process which comprises reaction to a compound of the general formula V

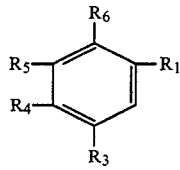

where $R_3$, $R_4$, $R_5$ and $R_6$ are as set forth above, with $HOCH_2CH$=$C(CH_3)_2$ in the presence of water and a water stable Friedel-Crafts catalyst such as acetic acid formic acid or polyphosphoric acid or phosphoric acid, known in the art. Alternatively,

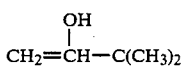

is employed as the unsaturated alcohol reactant.

Where the phenol ester is desired the ester group can be formed by techniques well known in the art.

There follow examples of the preparation compounds and their utility. These examples are to be considered illustrative rather than limiting. Throughout, all parts and percentages are by weight unless otherwise specified and all temperatures are degrees Centigrade unless otherwise specified.

EXAMPLE 1

Synthesis of 2-isopentenyl-4,5-dimethoxyphenol

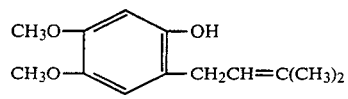

A mixture of 10 ml. of water, 4 ml. of formic acid and 3 grams of 3,4-dimethyloxyphenol was prepared and stirred in a water bath at about 80° C. There was then added dropwise at a fairly rapid rate 1.6 grams of Prenol (($CH_3)_2C$=CH—$CH_2OH$) and the reaction mixture was stirred for 30 minutes and allowed to come to room temperature. The reaction mixture was extracted with ether and the ether washed in the following sequence: water, saturated sodium bicarbonate solution, water and saturated sodium chloride solution. The ether extract was then dried over magnesium sulfate and then evaporated to yield 2.23 grams of material, which was fractionated on a florisil column to isolate the desired product.

EXAMPLE 2

Synthesis of 2-isopentenyl-4,5-dimethoxyphenyl acetate 100 mg. of the phenol of Example 1 was combined with 2 ml. of pyridine and 1 ml. of acetic anhydride for one hour. The reaction mixture was extracted with ether and the ether extract washed sequentially with water, 1NHCl, water and saturated salt solution then dried over sodium sulfate. Upon evaporation 0.11 grams of the acetate was recovered.

EXAMPLE 3

Synthesis of 2-isopentenyl-4-methoxy-5-ethoxyphenol 2 grams of 4-methoxy-5-ethoxyphenol was dissolved in 20 ml. of 28° formic acid solution with heating. The mixture was maintained in a water bath at 80° C. while there was added to the mixture, in a dropwise manner, 1.1 grams of $(CH_3)_2COHCH$=$CH_2$. After the addition the mixture was slowly stirred for an additional 30 minutes. The mixture was then cooled and extracted with ether. The ether extract was washed twice with water, three times with saturated sodium bicarbonate solution and once with a saturated salt solution. The ether layer was then dried over sodium sulfate and evaporated to yield 2.08 grams of material; GLC(OV,01) 190° showed product mixed with small amount of starting material. The product dissolved in a small amount of chloroform was added to a column containing 60 grams of Florisil and eluted as follows:

| Solvent | Amount of Eluant | Wt. of Product |
| --- | --- | --- |
| 10% $CHCl_3$/pet. ether | 200 ml | 0 |
| 20% $CHCl_3$/pet. ether | 100 ml | 0 |
| 20% $CHCl_3$/pet. ether | 100 ml | trace |
| 50% $CHCl_3$/pet. ether | 200 ml | .91 gm product and polar impurity |
| 50% $CHCl_3$/pet. ether | 200 ml | .45 gm product with only trace of starting phenol |
| 50% $CHCl_3$/pet. ether | 100 ml | .25 gm mostly starting |

| Solvent | Amount of Eluant | Wt. of Product |
|---|---|---|
| | | phenol |

INDUCTION OF PRECOCIOUS DEVELOPMENT

In accordance with the present invention, active isopentenyl substituted phenyl compounds were found to cause precocious maturation when applied to an immature insect. The juvenile hormone (JH) is a natural insect hormone which acts to keep the developing insect immature until it is ready to molt to the adult form. When maturation of the insect begins, the insect ceases to produce JH and the insect matures to the adult form. The compounds of the present invention have been found to stop the action of JH and cause the immature insect to undergo precocious maturation. For some insects the induced lack of JH causes such rapid maturation that the immature insect dies shortly prior to, or during the molting process. In other insects the lack of JH causes them to molt into miniature adults which completely avoids the tremendous feeding potential of the immature stages and results in tiny adults which are sterile, very fragile and which die soon after molting. The anti-juvenile hormone action can be overcome by the application of exogenous juvenile hormone, which indicates that the anti-juvenile hormone compounds act by interfering with the production of juvenile hormones.

Table I illustrates the induction of precocious maturation by contacting the milkweed bug with a chromene in accordance with the present invention. Other Hemiptera are also quite sensitive, and precocious metamorphesis has been induced in *Lygaeus kalmii* Stal and in *Dysdercus cingulatus*. Satisfactory results have not been obtained in inducing precocious metamorphesis in Holometabola.

STERILIZATION

In the normal adult insect, JH (or gonadotropic hormone) is produced again after molting to the adult form and is then necessary for the development of the insect ovaries. Treatment of adult insects with the compounds as described below in Table I was found to prevent or stop the action of JH and the insect ovaries failed to develop. If the insect ovaries were developed at the time of treatment, they rapidly regressed to the undeveloped state. In either event, reproduction was prevented. This technique has been successful with insects in the orders Hemiptera.

TABLE I

| | Induction of Precocious Metamorphasis In Immature Milkweed Bugs *Oncopeltus*[1] *Fasciatus* | | Sterilization of Adult Milkweed Bugs[2] | |
|---|---|---|---|---|
| | Dose ($\mu$g/cm$^2$) | % Precocious Adults | Dose ($\mu$g/cm$^2$) | % sterile |
| 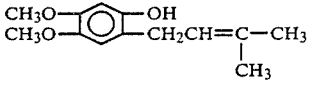 | 1.5 | 100% | 75.0 | 0 |
| 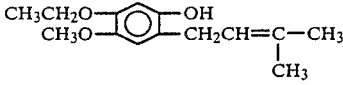 | 0.7 | 100% | 75.0[3] | 100 |

[1]Second instar nymphs were confined to a 9 cm. petri dish containing a residue of the test compound.
[2]Newly emerged adult female milkweed bugs were confined to a 9 cm. petri dish containing a residue of the test compound for 24 hours and then transferred to an untreated dish and held for 5 days at which time they were autopsied and the status of various development determined.
[3]Topical treatment of females with 500 $\mu$g/insect produced 70% sterility.

What is claimed is:
1. 2-isopentenyl-4-methoxy-5-ethoxyphenol.